United States Patent [19]
Chang et al.

[11] Patent Number: 4,888,354
[45] Date of Patent: Dec. 19, 1989

[54] SKIN PENETRATION ENHANCEMENT USING FREE BASE AND ACID ADDITION SALT COMBINATIONS OF ACTIVE AGENTS

[75] Inventors: Yunik Chang, Lakewood, N.J.; Dinesh C. Patel, Murray, Utah

[73] Assignee: Theratech, Inc., Salt Lake City, Utah

[21] Appl. No.: 136,115

[22] Filed: Dec. 21, 1987

[51] Int. Cl.⁴ ............................................. A01N 43/36
[52] U.S. Cl. ..................................... 514/424; 514/652; 514/657; 514/78; 514/272; 514/289; 514/343; 514/357; 514/617; 514/661
[58] Field of Search ................... 514/657, 424, 652, 78

[56] References Cited

U.S. PATENT DOCUMENTS 3,337,628  8/1967  Crowther et al. .................. 544/174
3,520,919  7/1970  Crowther et al. .................. 560/100
4,537,776  8/1985  Cooper ................................ 514/859
4,600,708  7/1986  Reuter et al. ........................ 514/657
4,731,384  3/1988  Dell et al. ............................ 514/658

OTHER PUBLICATIONS

"The Merck Index," 7740 Propranolol, p. 7743, 10th Ed., Windholz et al., Merck & Co. Inc., N.J., 1983.

Primary Examiner—William R. Dixon, Jr.
Assistant Examiner—Margaret B. Medley

[57] ABSTRACT

The invention is directed to compositions for topical application made up of active pharmaceutical permeants capable of existing in both free base and acid addition salt form. The permeants are present as a combination of both free base and acid addition salt forms. These combined forms provide skin penetration rates which are greater than the penetration rate of either the free base or acid addition salt forms utilized separately. The combined free base-acid addition salt permeants are formulated in a carrier vehicle which preferably also possesses skin penetration enhancement activity.

22 Claims, No Drawings

SKIN PENETRATION ENHANCEMENT USING FREE BASE AND ACID ADDITION SALT COMBINATIONS OF ACTIVE AGENTS

BACKGROUND OF THE INVENTION

This invention relates to compositions which enhance the penetration of pharmaceutically-active agents through the integument. More particularly, this invention relates to free base-acid addition salt combinations of active agents combined with vehicles which facilitate percutaneous and transepidermal delivery of pharmaceutically-active agents.

The resistance of the skin to being penetrated by pharmaceutically-active agents is well documented. As compared to mucosal tissues, the stratum corneum is compact and highly keratinized. The stratum corneum, although relatively thin, is compact and quite impermeable. Such impermeability of the skin is highly essential to the well being of a living organism in that it serves as a barrier to the ingress of pathogens and toxic materials, and the egress of physiologic fluids.

The impermeability of pharmaceutical agents through the skin is due to the nature of the very thin stratum corneum layer which is only 10–15 cells, i.e. about 10 microns thick. This layer is formed naturally by cells migrating toward the skin surface from the basal layer. Cells slowly move from the basal layer to the surface where they are sloughed off. As they progress toward the surface they become progressively more dehydrated and keratinized.

Because of the advantages of dermal application of pharmaceutically-active agents, various penetration enhancers have been sought. A penetration enhancer is generally considered to be one or more compounds which alter the skin as a barrier to increase the flux of a desired pharmaceutical permeant across the skin.

U.S. Pat. No. 4,537,776, Cooper, issued Aug. 27, 1985, contains an excellent summary of prior art and background information detailing the use of certain binary systems for permeant enhancement. Because of the completeness of that disclosure, the information and terminology utilized therein are incorporated herein by reference.

Similarly, European patent application No. 43,738, published Jan. 13, 1982, teaches using selected diols as solvents along with a broad category of cell-envelope disordering compounds for delivery of lipophilic pharmacologically-active compounds. Because of the detail in disclosing the cell-envelope disordering compounds and the diols, this disclosure of European patent application No. 43,738 is also incorporated herein by reference.

A binary system for enhancing metoclopramide penetration is disclosed in UK patent application GB No. 2,153,223 A, published Aug. 21, 1985 and consists of a monovalent alcohol ester of a C8–12 aliphatic monocarboxylic acid (unsaturated and/or branched if C18–32) or a C6–24 aliphatic monoalcohol (unsaturated and/or branched if C14–24) and an N-cyclic compound such as 2-pyrrolidone, N-methylpyrrolidone and the like.

Copending application. Ser. No. 930,764, filed Nov. 14, 1986 is drawn to binary composition consisting of a pharmaceutically-active agent dissolved in or admixed with a penetration-enhancing combination of one or more conventional cell envelope disordering compounds taught in the art cited above and a C2 or C3 alcohol. By using this binary mixture it was found that significant penetration of both hydrophilic and lipophilic permeants could be obtained and was often accompanied by reduced skin irritation.

Other enhancement vehicles, not necessarily associated with binary systems include DMSO or aqueous solutions of DMSO such as taught in Herschler, U.S. Pat. No. 3,551,554; Herschler, U.S. Pat. No. 3,711,602; and Herschler, U.S. Pat. No. 3,711,606, and the azones (n-substituted-alkyl-azacycloalkyl-2-ones) such as noted in Cooper, U.S. Pat. No. 4,557,943.

From the above prior art, it is evident that enhancement of penetration of active agents through the skin has been effected by selecting two primary categories of components, i.e., well-envelope disordering compounds and solvents as the vehicle. While active agents have been categorized as lipophilic or hydrophilic, little attention had been paid to means of manipulating the active agents per se to attain enhanced penetration through the skin barrier. Most prior art teachings are directed to means of enhancing the penetration of active ingredients present in an unionized free base or acid form. Recent examples show some binary enhancement systems enable active ingredients, in their salt form, to penetrate the stratum cornium at rates equal to or less than when in their free base form.

SUMMARY OF THE INVENTION

The present invention relates to compositions and methods for improving the penetration of pharmaceutically-active agents which are capable of existing in both free base and acid addition salt forms of pharmaceutically-active agent dissolved in, or admixed with, a carrier vehicle which may also be a penetration-enhancer.

By employing a free base-acid addition salt mixture of active ingredients, it has been found that penetration enhancement of the active ingredient is greatly improved as compared to use of either the free base or acid addition salt alone at the same concentration levels. In most cases, the rate of penetration is greater than the sum of the free base or acid addition salt when applied separately.

The invention is not limited to any specific category or categories of pharmaceutically active agents but is inclusive of all therapeutically active compounds capable of existing in both free base and acid addition salt form and their use as mixtures which are responsive by being incorporated into a carrier vehicle as more fully set forth herein.

Furthermore, the invention is not limited to any particular carrier vehicle. Preferably, penetration enhancement vehicles will be utilized. The binary vehicles described in numerous prior art patents and publications, as well as use of the solvents such as DMSO used separately are within the scope of the invention.

Also, the invention is drawn to treatment methods by means of which an effective amount of a free base and acid addition salt mixture combined with a carrier vehicle is topically applied to a human or animal subject.

DETAILED DESCRIPTION OF THE INVENTION

The following definitions, when used and as they apply to the present invention, are consistent with those contained in U.S. Pat. No. 4,537,776.

By "topical administration" or "topical application" is meant directly laying or spreading upon epidermal tissue, especially outer skin or membrane, including the skin or membrane of the oral or vaginal cavities.

By "safe and effective" is meant a sufficient amount of the mixed free base-acid addition salt permeant composition to provide the desired systemic effect and performance, or local activity, or both at a reasonable benefit/risk ratio attendant any medical treatment. Within the scope of sound medical judgment, the amount of permeant or active ingredient used will vary with the particular condition being treated, the severity of the condition, the duration of the treatment, the specific permeant mixture employed, its concentration, the condition of the patient, concurrent therapies being administered and other factors within the knowledge and expertise of the patient or the attending physician or other practitioner.

By "toxicologically- or pharmaceutically-acceptable" is meant the pharmaceutical actives (or permeants), as well as the other compatible drugs, medications or inert ingredients which the term describes, are suitable for use in contact with the tissues of humans and animals without undue toxicity, irritation, allergic response, and the like commensurate with a reasonable benefit/risk ratio.

By the terms "comprising" is meant that various other compatible drugs and medicaments, as well as inert ingredient, occlusive agents, and cosmetic vehicles, can be conjointly employed in the compositions and methods of this invention, as long as the desired mixture of free base and acid addition salt forms of pharmaceutically active permeants are used.

By "afflicted situs" is meant a localized area of pathology, discomfort, infection, inflammation or lesion, and the immediately surrounding area.

By "application situs" is meant a site suitable for topical application with or without the means of a mechanical sustained release device, path or dressing, e.g. behind the ear, on the arm, back, chest, stomach, leg, top of foot, etc.

By "penetration-enhancing" is meant that the combined free basic-acid addition salt mixtures of active permeants utilized separately or accompanied by a penetration enhancing carrier or vehicle provide marked transepidermal or percutaneous delivery of the active permeants, when compared to the use of the same amount of the active permeant used separately as either a free base or an acid addition salt under comparable conditions.

By "penetration enhancer", "penetration enhancement vehicle" or the like, is meant one or more compounds which alter the skin or membrane as a barrier or otherwise increase the flux of a desired permeant across the barrier.

As used herein, all percentages and ratios are by weight of the total composition unless otherwise specified.

The terms "permeant", "active", "pharmaceutical active", "pharmacological active", "pharmaceutical agent", "pharmacological agent", "pharmaceutically- or pharmacologically-active agent", "chemical agent", "therapeutic agent", "active drug" or words of a similar nature are used interchangeably herein.

By the term "free base" is meant a permeant which is charged or uncharged and contains protonatable functionalities.

By the term "acid addition salt" is meant a permeant free base which has been reacted with a pharmaceutically acceptable acid.

The compositions of this invention require, at a minimum, a mixture of a permeant in both the free base and acid addition salt forms preferably admixed with, or contained in, a carrier vehicle. The permeant base-acid addition salt mixture must be capable of producing systemic effects, or producing local activity when combined with the carrier vehicle. Preferably, the carrier vehicle will also possess penetration enhancement properties.

The composition may also contain other optional components which enhance their cosmetic appeal or acceptability, i.e., thickeners, pigments, fragrances, perfumes, and the like. The carrier vehicles utilized are preferably free of skin irritation characteristics. However, a permeant free base-acid addition salt mixture combined with a carrier vehicle may cause some irritation. Therefore, if desired, other components which tend to reduce skin irritation may be incorporated into the compositions as desired.

PENETRATION ENHANCEMENT VEHICLES

Because it is the combination of free bases and acid addition salts that result in the improved rate of permeant penetration through the stratum corneum or mucous membranes, the specific carrier vehicle and particularly the penetration enhancement vehicle utilized may be selected from a long list of prior art vehicles some of which are mentioned above and incorporated herein by reference. To specifically detail or enumerate that which is readily available in the art is not thought necessary. Therefore, rather than list specific agents, this specification shall list categories such as cell envelope disordering compounds and solvents.

Cell envelope disordering compounds are known in the art as being useful in topical pharmaceutical preparations. These compounds are thought to assist in skin penetration by disordering the lipid structure of the stratum corneum cell-envelopes. A comprehensive list of these compounds is described in European patent application No. 43,738, published June 13, 1982 which is incorporated herein by reference. Some additions to the structural formulae have been made to include certain glycerol esters. It is sufficient for purposes of this disclosure to state that the cell envelope disordering compounds are generally encompassed by the formula:

$$R-X$$

wherein R is a straight-chain alkyl of about 7 to 16 carbon atoms, a non-terminal alkenyl of about 7 to 22 carbon atoms, or a branched-chain alkyl of from about 13 to 22 carbon atoms, and X is $-OH$, $-COOCH_3$, $-COOC_2H_5$, $-OCOCH_3$, $-SOCH_3$, $-P(CH_3)_2O$, $-COOC_2H_4OC_2H_4OH$, $-COOCH(CHOH)_4CH_2OH$, $-COOCH_2CHOHCH_3$, $-COOCH_2CH(OR'')CH_2OR''$, $-(OCH_2CH_2)_mOH$, $-COOR'$, or $-CONR'_2$ where R' is $-H$, $-CH_3$, $-C_2H_5$, $-C_3H_7$ or $-C_2H_4OH$; R'' is $-H$, or a non-terminal alkenyl of about 7 to 22 carbon atoms; and m is 2-6; provided that when R'' is an alkenyl and X is $-OH$ or $-COOH$, at least one double bond is in the cis-configuration.

Suitable solvents include water; diols, such as propylene glycol and glycerol; mono-alcohols, such as ethanol, propanol, and higher alcohols; DMSO, dimethylformamide; 2-pyrrolidone; N-(2-hydroxyethyl) pyrrolidone, N-methylpyrrolidone, 1-dodecylazacycloheptan-2-one and other n-substituted-alkyl-azacycloalkyl-2-ones (azones) and the like.

The compositions of the invention typically contain from about 0 to 99.999% preferably from about 50 to 99.99% and most preferably, from about 75 to 99.99%, by weight of the overall composition, of the carrier vehicle. The exact percentages may be readily determined by one having ordinary skill in the art.

What is required is that, when a carrier vehicle is used, an effective amount of the active permeant free base-salt mixture be incorporated into the carrier vehicle with or without being combined with other ingredients.

PHARMACEUTICALLY-ACTIVE PERMEANTS

The invention encompasses the use of a broad range of pharmaceutically-active permeants which are capable of existing in both free base and acid addition salt forms. The compositions of this invention may be utilized in delivering active permeants to the "target" areas as mentioned in U.S. Pat. No. 4,537,776, i.e. (1) at the surface of the skin; (2) in the stratum corneum itself; (3) in the viable epidermis and upper dermis, just below the stratum corneum; (4) in the various glands and structures in and beneath the dermis (e.g., subcutaneous adipose, dermal vasculature); and/or (5) the general system (i.e. system effects).

In view of this, the invention is not limited to any specific type or class of active permeants provided they meet the above criteria of existing as free bases and acid addition salts. Based on the parameters contained herein, it is within the ability of one having ordinary skill in the art to determine which permeants can be utilized in these forms. Some routine experimentation or testing may be required to determine optimum conditions such as exact concentrations of permeants, ratio of free base to acid addition salt, and the like. Also, some permeants may work best with one particular class of carrier, including penetration enhancing, vehicles. The screening of all possible combinations and ratios of free base-acid addition salt mixtures of permeants has not been attempted as they can be empirically determined by one skilled in the art from the teaching contained herein.

However, based on the formulation of a representative sampling of diverse active free base-acid addition salt permeant mixtures, it is apparent that the use of permeants in such mixture forms will function to enhance the penetration of a broad spectrum of pharmaceutically-active permeants. Such agents include, without limitation, many of those mentioned in U.S. Pat. No. 4,537,776 such as antimicrobials, antibacterials, antibiotics, antimyobacterials, antimalerials, antimebics, anthelmintics, antifungals, antivirals, neoplastic agents, agents affecting the immune response, blood calcium regulators, peptide and protein hormones, agents useful in glucose regulation, antithrombotics and hemostatics, antihyperlipidemic agents, cardiac drugs, thyromimetic and antithyroid drugs, adrenergics, antihypertensive agents, cholinergics, anticholinergics, antispasmodics, antiulcer agents, skeletal and smooth muscle relaxants, histamine H2-receptor agonists and antagonists, general inhibitors of the allegeric response, antihistamines, local anesthetics, analgesics, antitussives, sedative-hypnotic agents, anticonvulsants, antipsychotics, anti-anxiety agents, antidepressant agents, anorexigenics, bone-active agents, antiarthritics, diagnostic agents and sun-screens. These agents can be used for systemic effect, local activity, or both, as appropriate. Examples of pharmaceutically-active permeants are well-known in the art and can be found listed in sources identified in U.S. Pat. No. 4,537,776 as well as others. For example, active agents, in approved commercially available formulations, their recommended dosages, adverse reactions, side effects and the like are listed in the annual publication of the *Physicians' Desk Reference,* published by Medical Economics Company, a division of Litton Industries, Inc.

The pharmaceutically-active permeants may be used in the compositions and methods of the present invention at any safe and effective level, or in any safe and effective amount. Dosages will obviously be a function of various variables, such as how active the agent is; how it is formulated; if used, how soluble it is in the penetration enhancing vehicle; how often it is to be applied; whether the use is to be topical (applied to the "afflicted situs") or systemic (applied to the "application situs"); whether two or more active permeants are to be combined; the particular patient being treated; and the like. In any event, the dosage will be the smallest that will achieve the desired result and the period of administration will be as short as possible to attain this result.

In general, means of application as taught in U.S. Pat. No. 4,537,776 are appropriate to the present invention. Dosages or levels of active permeants are limited by only what is safe and effective. If effective and tolerated, these may vary from about 0.001% to about 50% by weight of the total composition with levels of from about 0.01 to 25% being preferred. Levels from about 0.05 to 10% being especially preferred. However, for some active permeants, it may be required to use more or less than stated above to attain the desired results. Hence, the invention is not directed to any particular amount of active ingredient as long as they are safe and effective.

A compendium of active permeants is contained in U.S. Pat. No. 4,537,776 and published European patent application No. 43,738 and incorporated herein by reference. However, for purposes of illustration, a concise listing of active agents follows.

Typical antihypertensive agents which may be utilized include, without limitation, minoxidil, propranolol, clonidine, prazosin, hydralazine, nifedipine, diltriazem and nicardipine.

Exemplary of a diuretic permeant is amiloride.

A broad range of opioid analgesics and antagonists may be utilized including, without limitation, morphine, codeine, methadone, levorphanol, meperidine and naloxone.

Exemplary cholinergics include pilocarpine, arecoline, and muscarine.

Anticholinesterase agents are inclusive of physostigmine and neostigmine.

Antimuscarinic agents include atropine and scopolamine.

Sympathomimetic agents which may be used are epinephrine, dopamine and ephedrine. Adrenergic blocking agents within this class include phenoxybenzamine, phentolamine, tolazoline, propranolol, pindolol and timolol.

Inclusive of ganglionic stimulating agents are nicotine and lobeline and of ganglionic blocking agents is mecamylamine.

Typical of neuromuscular blocking agents are tubocurarine and succinylcholine and of local anesthetics are lidocaine and procaine.

Permeants used in the treatment of mental and emotional states include hypnotics and sedatives such as flurazepam and chlordiazepoxide; antipsychotic agents such as chlorpromazine, fluphenazine and trifluoperazine and antidepressants such as amitriptyline, imipramine, trimipramine and desimipramine.

Drugs used to treat Parkinson's Disease include amantadine, bromocriptine and benztropine, methyldopa and dopamine.

Antiemetic permeants include metoclopramide, chlorpromazine and prochlorperazine.

Central nervous stimulants include agents such as methylphenidate, doxapram and theophylline.

Inclusive of antihistamines and diphenhydramine, chlorpheniramine, hydroxyzine, cimetidine and ranitidine.

Antiarrhythmic agents which may be utilized include procaineamide, lidocaine and verapamil.

An anthelmintic agent is arecoline.

Antitussive agents are dextromethorphan and codeine.

The above listed active permeants are listed in their free base form. However, all may be used to form pharmaceutically acceptable acid addition salts of inorganic and organic acids such as hydrochloric, hydrobromic, hydroiodic, phosphoric, sulfuric, nitric, sulfamic, citric, lactic, maleic, pyruvic, oxalic, succinic, tartaric, cinnamic, acetic, trifluoroacetic, benzoic, salicylic, gluconic, ascorbic and related acids. The above lists are not exhaustive and there are other pharmaceutically active free base permeants not specifically disclosed which are also within the scope of the invention. Also, there may be other pharmaceutically acceptable acids which may be used to form acid addition salts.

What is surprising is that by combining these permeants in their free base and acid addition salt form as a mixture, the flux or rate of penetration across skin or membrane barriers is significantly improved. In most cases, the improvement is synergistic, i.e. more than additive. The ratio of free base to salt may vary from permeant to permeant. A stoichiometric or 1:1 molar ratio is probably optimal. However, the ratio can vary within wide limits with varying degrees of improvement. Weights from 1:20 to 20:1 of free base to acid addition salt are considered exemplary of the outer ratio limits. However, ratios of 1:10 to 10:1 are probably more appropriate with ratios of 1:5 to 5:1 being preferred.

In its most basic or fundamental embodiment, a mixture of free base and acid addition salt permeants may be formulated with or without a carrier and applied to the skin or mucous membranes to be treated.

However, in preparing formulations for actual use, it may be desirable to add other components such as excipients, dyes, perfumes, fragrances, opacifiers, thickening agents, preservatives, anti-oxidants, gelling agents, surfactants and stabilizers. For example, when forming gels or creams, it may be desirable to add significant amounts of water, i.e. up to 50% in some cases for gels. Such materials, when added, should not unduly interfere with the penetration enhancement of these compositions. Such formula modifications to improve cosmetic acceptability are well within the skill of workers in the art.

In most instances the inclusion or use of a carrier vehicle and particularly a penetration enhancement vehicle will be beneficial. The amount of these vehicles will depend entirely upon the vehicle used and the permeants involved. Other ingredients should also be taken into consideration. What is important is that sufficient permeant, in both free base and acid addition salt form, be used to achieve the desired result and the appropriate amount of vehicles or other adjuvants be used to assist in accomplishing that result.

METHOD OF USE

In any form of medical practice, there are many variables which affect the particular treatment regimen. In that regard, the final diagnosis and treatment is left to the expertise of the practitioner and patient. As previously stated, in clinical practice, it is the goal that the dosage of any active permeant be as small as possible to achieve the result desired and that the adminstration of the permeant be as short as possible. That is one of the advantages of the present invention. By the enhanced penetration obtained by the combination of the free base and acid addition salt forms of the same permeant, smaller overall amounts may be utilized to attain the same flux or rate of penetration. Obviously, it is imperative that the amount of active ingredient utilized is a safe and effective amount whether applied to an afflicted situs or an application situs. By utilizing the combined free base and acid addition salt forms more effectiveness with a greater degree of safety can be realized. When local treatment is desired, the compositions are applied to the afflicted situs. When systemic treatment is desired, the compositions are applied to an application situs, preferably from a sustained release device such as a patch, bandage, web, film or the like. When both local and systemic treatments are indicated, the compositions can be applied at both the afflicted situs and application situs, or both. The selection of active permeant or combination or permeants, are necessarily left to the skill of the practitioner provided the parameters outlined herein are followed.

The dosage, rate of application, place of application, and other treatment parameters are generally to be determined by an experienced practitioner depending upon the permeant combination, condition being treated and the like. What is a safe and effective amount of any ingredient will obviously depend upon the active ingredient being used, the site of application, the degee of enhancement obtained by means of using a combined free base and acid addition salt form and the effectiveness of any penetration enhancer that may be used and other parameters outlined herein.

A practitioner being skilled in the art will be able to determine the application parameters of each specific formulation based on the needs of each patient.

EXAMPLES

The following examples demonstrate the improvement in penetration enhancement that is obtained by utilizing active permeants as a mixture of free base and acid addition salt forms. In conducting these tests, human skin consisting of heat-separated abdominal epidermis was placed in a standard Franz diffusion apparatus in a horizontal position between a lower, capped diffusion cell and an upper open cell. A normal saline solution was added to the lower diffusion cell in contact with the subcutaneous side of the skin. The test composition, consisting of a solution containing a combined free base-acid addition salt mixture of the drug being tested and formulated as indicated in each example, was added to the diffusion cell in contact with the upper or epidermal side of the skin.

The cell assembly was kept at a constant-temperature room at about 32° C. At predetermined intervals the diffusate from the cell on the subcutaneous side of the skin was withdrawn and the amount of drug in the diffusate was measured using standard analytical techniques. Each test was run using a separate skin sample. The results are reported in terms of flux [msg/cm2/day].

EXAMPLE I

This example shows the improved flux utilizing various classes of active permeants, propranolol, chlorpheniramine, and metoclopramide, contained in a vehicle consisting of 75% methyl laurate and 25% isopropanol. Solutions were prepared, containing free base, acid addition salt and combinations of free base and acid addition salt. The base and acid addition salt solutions were prepared by adding equal amounts of the free base and salt to separate vehicle solutions and then taking aliquot portions of each free base and acid addition salt solution and combining them. Since the combined solution was made by combining equal volumes of free base and acid addition salt solution, the predicted skin flux of the active component should be an average of the flux obtained for the free base and acid addition salts tested separately.

The concentrations utilized and results obtained are shown in Table I as follows:

TABLE I

| | | FLUX[mcg/cm2/day] | | | |
|---|---|---|---|---|---|
| | | | | Combined Base and Salt | |
| Test No. | Active Ingredient | Salt | Free Base | Actual | Predicted* |
| I-A | Propranolol | 7,898(1) (0.1 g/ml) | 4,265 (0.1 g/ml) | 25,868 (0.05 g/ml salt + 0.05 g/ml free base) | 6,082 |
| I-B | Chlorphenicamine | 8,114(2) (0.25 g/ml) | 16,502 (0.25 g/ml) | 49,537 (0.125 g/ml salt + 0.125 g/ml free base) | 12,456 |
| I-C | Metoctopramide | 291(1) (0.05 g/ml) | 1,210 (0.05 g/ml) | 2,075 (0.025 g/ml salt + 0.025 g/ml free base) | 751 |

(1) = hydrochloride salt
(2) = maleate salt
*Predicted flux = $\frac{\text{Salt Flux + Base Flux}}{2}$ These results clearly show that by combining both free base and acid addition forms of these permeants, the flux is greatly increased over the rate realized when the free base or acid addition salts forms are used separately.

EXAMPLE II

The procedure of Example I was followed utilizing propranolol and its hydrochloride acid addition salt as the permeant combination with the exception that the carrier vehicle was 75% glycerol dioleate and 25% isopropanol. The results are shown in Table II as follows:

TABLE II

| | | FLUX [mcg/cm2/day] | | | |
|---|---|---|---|---|---|
| | | | | Combined Base and HCl Salt | |
| Test No. | Active Ingredient | HCl Salt | Free Base | Actual | Predicted* |
| II-A | Propranolol | 618 (0.05 g/ml) | 624 (0.05 g/ml) | 1,997 (0.025 g/ml salt + 0.025 g/ml free base | 621 |

*Predicted flux = $\frac{\text{Salt Flux + Base Flux}}{2}$

Again, the results clearly show the superior flux obtained from the use of a combined free base-acid addition salt mixture as compared to each component used separately.

EXAMPLE III

In order to show that acid permeants and their salt forms do not function in combined form to provide enhance penetration, a vehicle consisting of 70% glycerol dioleate and 30% isopropanol was prepared as in Example I and divided into two portions. Sufficient salicylic acid was added to one portion to provide a concentration of 100 mg/ml. A saturated solution of sodium salicylate also containing 100 mg/ml was prepared. Aliquot portion of each solution were combined as in Example I. The skin flux rates of the acid, salt and combined solutions are shown in Table III as follows:

TABLE III

| | | FLUX [mcg/cm2/day] | | | |
|---|---|---|---|---|---|
| | | | | Combined Acid and Na Salt | |
| Test No. | Active Ingredient | Na Salt | Free Acid | Actual | Predicted* |
| III-A | Salicylic Acid | 64.9 (0.1 g/ml) | 68.7 (0.1 g/ml) | 36.3 (0.05 g/ml Na salt + 0.05 g/ml free acid) | 66.8 |

*Predicted flux = $\frac{\text{Salt Flux + Acid Flux}}{2}$

These results just as clearly show that combining acid permeants and their salts do not result in the same flux increase as obtained in Examples I and II.

EXAMPLE IV

The following formulations in Table IV are exemplary of other combinations of free bases and their acid addition salts, with a suitable carrier vehicle, which are within the scope of this invention. They are illustrative only and are not intended to define or limit the scope of the invention. The compositions can be conventionally formulated by adding the desired amounts of free base and acid addition salt to the carrier vehicle.

TABLE IV

| Permeant | Salt Form (mg/ml) | Free Base (mg/ml) | Carrier Vehicle (% W) A | B | C |
|---|---|---|---|---|---|
| flurazepam | HCl (0.10) | (0.10) | 80(OA) | 20(EtOH) | — |
| nicotine | tartarate (0.85) | (0.15) | 20(GMO) | 70(iPrOH) | 10(H2O) |
| morphine | sulfate (0.01) | (0.01) | 75(ML) | 25(EtOH) | — |
| levorphanol | tartarate (0.01) | (0.01) | 25(GDO) | 75(EtOH) | — |

TABLE IV-continued

| Permeant | Salt Form (mg/ml) | Free Base (mg/ml) | Carrier Vehicle (% W) A | B | C |
|---|---|---|---|---|---|
| minoxidil | HCl (0.10) | (0.10) | 95(PG) | 5(OA) | — |
| nifedipine | HCl (0.10) | (0.05) | 60(DMSO) | 40(H2O) | — |
| arecoline | HBr (0.10) | (0.10) | 25(OA) | 50(EtOH) | 25(PG) |
| atropine | sulfate (0.01) | (0.05) | 75(GDO) | 25(iPrOH) | — |
| pinodolol | HCl (0.05) | (0.05) | 75(ML) | 25(EtOH) | — |
| timolol | HCl (0.10) | (0.20) | 60(GDO) | 40(PrOH) | — |
| lidocaine | HCl (0.025) | (0.05) | 5(Azone) | 95(PG) | — |
| flephenazine | HCl (0.01) | (0.04) | 75(GNO) | 20(EtOH) | 5(H2O) |
| methylphenidate | HCl (0.025) | (0.025) | 50(GDO) | 50(iPrOH) | — |
| bromocriptine | mesylate (0.01) | (0.01) | 75(EtOH) | 20(GMO) | 5(H2O) |
| mecamylamine | HCL (0.10) | (0.05) | 75(iPrOH) | 25(GDO) | — |
| cimetidine | HCl (0.10) | (0.10) | 75(DMSO) | 25(H2O) | — |
| verapamil | HCl (0.05) | (0.05) | 70(EtOH) | 15(PG) | 15 (Azone) |
| imipramine | HCl (0.25) | (0.25) | 75(IPrOH) | 25(OA) | — |
| trimipramine | maleate (0.20) | (0.30) | 70(DMSO) | 30(H2O) | — |
| amaniadine | HCl (0.25) | (0.25) | 75(iPrOH) | 25(SGO) | — |

OA = oleic acid,
EtOH = ethanol,
iPrOH = isopropanol,
GMO = glycerol monooleate,
GDO = glycerol dioleate
ME = methyl laurate,
PG = propylene glycol,
PrOH = propanol,
DMSO = dimethyl sulfoxide While the above examples illustrate numerous embodiments of the invention, the scope of the invention is limited only by the operability of the mixtures of free base permeants and their acid addition salts. It is to these mixtures and the unexpected property of enhanced skin penetration possessed by these mixtures that the present invention is drawn. It is, therefore, limited in scope only by the appended claims and their functional equivalents.

We claim:

1. A penetration-enhancing pharmaceutical composition for topical application containing an active permeant which exists in both free base and acid addition salt forms comprising:
    (a) about 0.001 to 50% by weight of said permeant which is present as a mixture consisting of both free base and acid addition salt forms wherein the weight ratio of free base to acid addition salt in said mixture is between about 1:20 and 20:1 and wherein said acid addition salt is formed by reacting the free base with an acid selected from the group consisting of hydrochloric, hydrobromic, hydroiodic, phosphoric, sulfuric, nitric, sulfamic, citric, lactic, maleic, pyruvic, oxalic, succinic, tartaric, cinnamic, acetic, trifluoroacetic, benzoic, salicylic, gluconic, ascorbic and related pharmaceutically acceptable acids; and
    (b) 50 to 99.999% by weight of a pharmaceutically acceptable carrier.

2. A penetration-enhancing composition for topical application according to claim 1 wherein the weight ratio of free base to acid addition salt forms of the permeant is between about 1:10 and 10:1.

3. A composition according to claim 1 wherein the active pharmaceutical permeant is a member selected from the group consisting of antimicrobials, antibacterials, antibiotics, antimyobacterials, antimalerials, antimebics, anthelmintics, antifungals, antivirals, neoplastic agents, agents affecting the immune response, blood calcium regulators, peptide and protein hormones, agents useful in glucose regulation, antithrombotics and hemostatics, antihyperlipidemic agents, cardiac drugs, thyromimetic and antithyroid drugs, adrenergics, antihypertensive agents, cholinergics, anticholinergics, antispasmodics, antiulcer agents, skeletal and smooth muscle relaxants, histamine H2-receptor agonists and antagonists, general inhibitors of the allergic response, antihistamines, local anesthetics, analgesics, antitussives, sedative-hypnotic agents, anticonvulsants, antipsychotics, anti-anxiety agents, antidepressant agents, anorexigenics, bone-active agents, antiarthritics, diagnostic agents, sunscreen agents and compatible mixtures thereof.

4. A penetration-enhancing composition for topical application according to claim 1 wherein the permeant comprises a free base form of propranolol and an acid addition salt of propranolol.

5. A penetration-enhancing composition according to claim 4 wherein the acid addition salt of propranolol is propranolol hydrochloride.

6. A penetration-enhancing composition for topical application according to claim 1 wherein the permeant comprises a free base form of chlorpheniramine and an acid addition salt of chlorpheniramine.

7. A penetration-enhancing composition according to claim 6 wherein the acid addition salt of chlorpheniramine is chlorpheniramine maleate.

8. A penetration-enhancing composition for topical application according to claim 1 wherein the permeant comprises a free base form of metoclopramide and an acid addition salt of metaclopramide.

9. A penetration-enhancing composition according to claim 8 wherein the acid addition salt of metoclopramide is metoclopramide hydrochloride.

10. A penetration-enhancing composition for topical application according to claim 1 wherein the permeant comprises a free base form of nicotine and an acid addition salt of nicotine.

11. A penetration-enhancing composition according to claim 10 wherein the acid addition salt of nicotine is nicotine tartrate.

12. A penetation-enhancing composition for topical application according to claim 1 wherein the permeant compries a free base form of morphine and an acid addition salt of morphine.

13. A penetration-enhancing composition according to claim 12 wherein the acid addition salt of morphine is morphine sulfate.

14. A penetration-enhancing composition for topical application according to claim 1 wherein the permeant comprises a free base form of minoxidil and an acid addition salt of minoxidil.

15. A penetration-enhancing composition according to claim 14 wherein the acid addition salt of minoxidil is minoxidil hydrochloride.

16. A penetration-enhancing composition for topical application according to claim 1 wherein the permeant comprises a free base form of mecamylamine and an acid addition salt of mecamylamine.

17. A penetration-enhancing composition according to claim 16 wherein the acid addition salt of mecamylamine is mecamylamine hydrochloride.

18. A penetration-enhancing composition for topical application according to claim 1 wherein the permeant comprises a free base form of dextromethorphan and an acid addition salt of dextromethorphan.

19. A penetration-enhancing composition according to claim 18 wherein the acid addition salt of dextromethorphan is dextromethorphan hydrobromide.

20. A method for enhancing the rate of penetration of an active pharmaceutical permeant, capable of existing in both free base and acid addition salt forms, across the skin or mucous membrane barrier of a subject which comprises topically applying to the skin or mucous membranes of said subject a safe and effective amount of a composition comprising:
(a) about 0.001 to 50% by weight of said permeant which is present as a mixture consisting of both free base and acid addition salt forms wherein the weight ratio of free base to acid addition salt in said mixture is between about 1:20 and 20:1 and wherein said acid addition salt is formed by reacting the free base with an acid selected from the group consisting of hydrochloric, hydrobromic, hydroiodic, phosphoric, sulfuric, nitric, sulfamic, citric, lactic, maleic, pyruvic, oxalic, succinic, tartaric, cinnamic, acetic, trifluoroacetic, benzoic, salicylic, gluconic, ascorbic and related pharmaceutically acceptable acids; and
(b) 50 to 99.999% by weight of a pharmaceutically acceptable carrier.

21. A method according to claim 20 wherein the weight ratio of free base to acid addition salt forms of the permeant being applied is between about 1:10 to 10:1.

22. A method according to claim 1 wherein the active pharmaceutical permeant being applied is a free base-acid addition salt combination of a permeant member selected from the group consisting of antimicrobials, antibacterials, antibiotics, antimyobacterials, antimalerials, antimebics, anthelmintics, antifungals, antivirals, neoplastic agents, agents affecting the immune response, blood calcium regulators, peptide and protein hormones, agents useful in glucose regulation, antithrombotics and hemostatics, antihyperlipidemic agents, cardiac drugs, thyromimetic and antithyroid drugs, adrenergics, antihypertensive agents, cholinergics, anticholinergics, antispasmodics, antiulcer agents, skeletal and smooth muscle relaxants, histamine H2-receptor agonists and antagonists, general inhibitors of the allergic response, antihistamines, local anesthetics, analgesics, antitussives, sedative-hypnotic agents, anticonvulsants, antipsychotics, anti-anxiety agents, antidepressant agents, anorexigenics, bone-active agents, antiarthritics, diagnostic agents, sunscreen agents and compatible mixtures thereof.

* * * * *